United States Patent
Greathouse et al.

(10) Patent No.: US 9,492,421 B1
(45) Date of Patent: Nov. 15, 2016

(54) NUTRITIONAL SUPPLEMENTS FOR TREATMENT OF IRON DEFICIENCY ANEMIA

(71) Applicants: Kenneth R. Greathouse, Los Altos, CA (US); Rhett Sean Daniels, Santa Monica, CA (US)

(72) Inventors: Kenneth R. Greathouse, Los Altos, CA (US); Rhett Sean Daniels, Santa Monica, CA (US)

(73) Assignee: Argent Development Group, LLC, Mountain View, CA (US)

( * ) Notice: Subject to any disclaimer, the term of this patent is extended or adjusted under 35 U.S.C. 154(b) by 54 days.

(21) Appl. No.: 14/121,768

(22) Filed: Oct. 16, 2014

Related U.S. Application Data

(60) Provisional application No. 61/962,691, filed on Nov. 14, 2013.

(51) Int. Cl.
    *A01N 59/20* (2006.01)
    *A61K 33/34* (2006.01)
    *A61K 31/295* (2006.01)

(52) U.S. Cl.
    CPC .................. *A61K 31/295* (2013.01)

(58) Field of Classification Search
    None
    See application file for complete search history.

(56) References Cited

U.S. PATENT DOCUMENTS

| | | | |
|---|---|---|---|
| 4,725,427 A | 2/1988 | Ashmead et al. | |
| 4,994,283 A * | 2/1991 | Mehansho | A23L 1/304 424/439 |
| 5,292,538 A | 3/1994 | Paul et al. | |
| 5,516,925 A | 5/1996 | Pedersen et al. | |
| 5,795,873 A | 8/1998 | Allen | |
| 5,817,659 A | 10/1998 | Muller et al. | |
| 5,869,084 A | 2/1999 | Paradissis et al. | |
| 5,932,624 A | 8/1999 | Herbert | |
| 5,997,915 A | 12/1999 | Bailey et al. | |
| 6,160,116 A | 12/2000 | Mueller et al. | |
| 6,254,904 B1 | 7/2001 | Bailey | |
| 6,271,374 B1 | 8/2001 | Muller et al. | |
| 6,299,896 B1 | 10/2001 | Cooper et al. | |
| 6,361,800 B1 | 3/2002 | Cooper et al. | |
| 6,368,621 B1 | 4/2002 | Engel et al. | |
| 6,441,168 B1 | 8/2002 | Muller et al. | |
| 6,458,981 B1 | 10/2002 | Ashmead et al. | |
| 6,488,956 B1 | 12/2002 | Paradissis et al. | |
| 6,521,247 B1 | 2/2003 | de Vries | |
| 6,528,496 B1 | 3/2003 | Allen et al. | |
| 6,673,381 B2 | 1/2004 | Bailey et al. | |
| 6,716,814 B2 | 4/2004 | Ericson et al. | |
| 6,808,725 B2 | 10/2004 | Bailey et al. | |
| 6,953,888 B2 | 10/2005 | Livshitz et al. | |
| 7,172,778 B2 | 2/2007 | Bailey et al. | |
| 7,341,708 B1 * | 3/2008 | Miroshnychenko | A23L 1/3051 424/1.11 |
| 7,674,490 B2 | 3/2010 | Bailey et al. | |
| 7,704,542 B2 | 4/2010 | Bydlon et al. | |
| 7,964,189 B1 | 6/2011 | Morrison et al. | |
| 7,981,858 B1 | 7/2011 | Lang | |
| 7,994,217 B2 | 8/2011 | Nidamarty et al. | |
| 8,007,846 B2 | 8/2011 | Thompson et al. | |
| 8,007,853 B2 | 8/2011 | Bydlon et al. | |
| 8,075,910 B2 | 12/2011 | Schramm et al. | |
| 8,168,611 B1 * | 5/2012 | Perrin | A23L 1/3006 514/168 |
| 8,173,160 B2 | 5/2012 | Schramm et al. | |
| 8,178,709 B2 | 5/2012 | Nelson et al. | |
| 8,183,227 B1 | 5/2012 | Perrin et al. | |
| 8,383,165 B1 * | 2/2013 | Andrews | A61K 36/87 424/725 |
| 8,425,956 B2 | 4/2013 | Thompson et al. | |
| 8,454,950 B2 | 6/2013 | Haschke et al. | |
| 8,454,951 B2 | 6/2013 | Morrison et al. | |
| 8,470,352 B2 | 6/2013 | Liu et al. | |
| 8,491,937 B2 | 7/2013 | Goldberg et al. | |
| 8,535,659 B1 | 9/2013 | Morrison et al. | |
| 8,535,660 B1 * | 9/2013 | Morrison | A61K 31/07 424/408 |
| 8,637,061 B2 | 1/2014 | Liu et al. | |
| 2006/0134227 A1 | 6/2006 | Bortz et al. | |
| 2007/0270591 A1 * | 11/2007 | Ashmead | C07F 15/025 548/101 |
| 2008/0031976 A1 * | 2/2008 | Evenstad | A61K 31/519 424/646 |
| 2009/0124572 A1 | 5/2009 | Nelson | |
| 2012/0100123 A1 | 4/2012 | Gonzalez et al. | |
| 2012/0189692 A1 * | 7/2012 | Cullen | A61K 33/26 424/452 |
| 2013/0338039 A1 * | 12/2013 | Mazed | G01N 21/6454 506/16 |

OTHER PUBLICATIONS

Drugs.com ("Vitamin B Complex/Vitamin C/Folic Acid/Iron/Zinc" "http://web.archive.org/web/20100418094511/http://www.drugs.com/cdi/vitamin-b-complex-vitamin-c-folic-acid-iron-zinc.html").*
Swanson.com ("Effer-C Effervescent Drink Mix https://web.archive.org/web/20121104061555/http://www.swansonvitamins.com/now-foods-effer-c-effervescent-drink-mix-elderberry-30-pkts").*
Aguilar (Scientific Opinion of the Panel on Food Additives and Nutrient Sources added to Food on a request from the Commission on adenosylcobalamin and methylcobalamin as sources for Vitamin B12. The EFSA Journal (2008) xxx, 1-21; © European Food Safety Authority, 2008).*
Mervue (http://www.agrobest.cz/img/pdf/products/ru/detail/Calf_Aid_letak.pdf).*
Lafeber (http://www.shopthebirdshoppe.com/shop/item.aspx?itemid=62).*
Vitazan (http://www.nhpassist.com/products/vitazan-professional/multi-power-240-vegcaps).*
Brewer (GB 2289406 A).*

\* cited by examiner

*Primary Examiner* — Robert A Wax
*Assistant Examiner* — Quanglong Truong
(74) *Attorney, Agent, or Firm* — Joseph I. Hirsch

(57) ABSTRACT

The present invention relates to nutritional supplements to be administered to, or to be taken by, people who are subject, or thought to be subject to, iron deficiency anemia. The nutritional supplements of this invention have a unique formulation of iron and folic acid-related materials in addition to certain other vitamins and minerals and a nutritionally acceptable carrier therefor. The invention describes specific nutritional supplements for the use set forth above.

10 Claims, No Drawings

NUTRITIONAL SUPPLEMENTS FOR TREATMENT OF IRON DEFICIENCY ANEMIA

CROSS-REFERENCE TO RELATED APPLICATION

This application is based upon, and claims priority from, U.S. provisional application Ser. No. 61/962,691, filed Nov. 14, 2013, the disclosure of which is incorporated herein by this reference.

FIELD OF THE INVENTION

The present invention relates to nutritional supplements to be administered to, or to be taken by, people suffering from iron deficiency anemia.

BACKGROUND OF THE INVENTION

The most common cause of anemia is iron deficiency, which occurs in both men and women. This may result from gastrointestinal blood loss due to drug therapy (often in the case of use of aspirin and non-steroidal anti-inflammatory drugs). In adolescents, rapid growth may outpace dietary intake of iron, and result in iron deficiency anemia without disease or grossly abnormal diet. In women of childbearing age, heavy or long menstrual periods can also cause iron deficiency anemia.

Without iron supplementation, iron deficiency anemia occurs in many pregnant women because their iron stores need to serve their own increased blood volume as well as be a source of hemoglobin for the growing fetus. While minerals and vitamins can be obtained through diet, it is known that less than 10% of average Americans consume a nutritious diet sufficient to supply these materials. This can, with respect to pregnant women, increase the risk of maternal and/or fetal mortality, premature delivery and low birth weight, and other associated complications, both before and after delivery.

Especially in adults over the age of 50, iron deficiency anemia is often a sign of other diseases in the gastrointestinal tract, such as chronic bleeding from any cause (for example, a colon cancer) that causes loss of blood in the stool. Such loss is often undetectable, except with special testing. In adults, 60% of patients with iron deficiency anemia have underlying gastrointestinal disorders leading to chronic blood loss, and this percentage increases with patient age.

Iron deficiency anemia also affects people having chronic diseases, such as kidney disease, inflammatory bowel disease, cancer, HIV, and diabetes.

Many supplements called hemetinics have been proposed and/or are currently being marketed in the United States to overcome the iron deficiency anemia. See, for example, Helenek et al. U.S. Pat. No. 7,754,702; Venkataraman et al. U.S. Pat. No. 7,785,527 and U.S. Pat. No. 8,080,520; Nidamarty et al. U.S. Pat. No. 7,994,217; Connor et al. U.S. Pat. No. 8,071,542; and Nelson et al. U.S. Pat. No. 8,178,709. Prenatal supplements with iron are described in Morrison et al. U.S. Pat. No. 7,964,189 and U.S. Pat. No. 8,454,951. Heme-iron for example, while highly bioavailable from meat and animal products, is not always the best option for iron supplementation. However, commonly used forms of non-heme iron (from sources like vegetables and iron supplements), cause gastrointestinal distress, which undermines individual or patient compliance. While ingredients used in currently available supplements may not do any harm, in the sense that the body will eliminate in one way or another that which is not needed, there is a preference, and it is our desire, to set forth unique nutritional supplement that have those, and only those, ingredients that serve necessary and beneficial purposes related to treating iron deficiency anemia.

BRIEF SUMMARY OF THE INVENTION

The present invention relates to unique nutritional supplements to be administered to, or to be taken by, people with iron deficiency anemia.

The unique nutritional supplements of the present invention are particularly suited for being administered to, or to be taken by, people suffering from iron deficiency anemia and are free or substantially free (as those words are defined below) of any other added vitamins and minerals.

The nutritional supplements of the present invention consist essentially of a daily dose of nutritionally effective amounts of:

iron administered in the form of a nutritionally acceptable iron amino acid chelate, one or more materials selected from the group consisting of folic acid, a citrated folic acid material, folinic acid, the methylfolate derivatives thereof and the nutritionally acceptable salts thereof, Vitamin $B_1$, Vitamin $B_{12}$, Vitamin C, copper, zinc, optionally magnesium, optionally one or more of the vitamins selected from the group consisting of Vitamin A, Vitamin $B_2$, Vitamin $B_3$ and Vitamin $B_6$, and a nutritionally acceptable carrier therefor.

In one embodiment of the present invention, the nutritional supplements consist essentially of a daily dose of:

about 50 mg to about 150 mg of elemental iron administered in the form of a nutritionally acceptable iron amino acid chelate, about 0.1 mg to about 5 mg of one or more materials selected from the group consisting of folic acid, folinic acid, the methylfolate derivatives thereof, the nutritionally acceptable salts thereof, and an amount of a citrated folic acid material containing about 0.1 mg to about 5 mg of folic acid, preferably about 1 mg of folic acid, about 10 mcg to about 1,500 mcg of Vitamin $B_1$, about 100 mcg to about 5,000 mcg of Vitamin $B_{12}$, about 10 mg to about 100 mg of Vitamin C, about 1 mg to about 3 mg of elemental copper about 1 mg to about 30 mg of elemental zinc, optionally about 0.1 mg to about 10 mg of elemental magnesium, optionally about 200 IU to about 2,000 IU of Vitamin A, optionally about 10 mcg to about 1,500 mcg of Vitamin $B_2$, optionally about 10 mcg to about 1,500 mcg of Vitamin $B_3$, optionally about 0.5 mg to about 5 mg of Vitamin $B_6$, and a nutritionally acceptable carrier therefor.

In another embodiment of the present invention, the nutritional supplement consists essentially of a daily dose of:

about 80 mg to about 100 mg of elemental iron in the form of a nutritionally acceptable iron amino acid chelate, about 1 mg to about 2.5 mg of one or more materials selected from the group consisting of folic acid, folinic acid, the methylfolate derivatives thereof, and the nutritionally acceptable salts thereof, and an amount of a citrated folic acid material containing about 1 mg to about 2.5 mg of folic acid, preferably about 1 mg of folic acid, about 400 IU to about 1,000 IU of Vitamin A,
about 20 mcg to about 625 mcg of Vitamin $B_1$,
about 20 mcg to about 625 mcg of Vitamin $B_2$,
about 20 mcg to about 625 mcg of Vitamin $B_3$,
about 0.5 mg to about 1.5 mg of Vitamin $B_6$,
about 400 mcg to about 600 mcg of Vitamin $B_{12}$,
about 30 mg to about 70 mg of Vitamin C,
about 1 mg to about 3 mg of elemental copper,
about 5 mg to about 15 mg of elemental zinc,
optionally about 0.2 mg to about 5 mg of elemental magnesium, and
a nutritionally acceptable carrier therefor.

In an exemplary embodiment of the present invention, the nutritional supplements include a daily dose of:

about 80 mg to about 100 mg of elemental iron administered in the form of a nutritionally acceptable iron amino acid chelate, about 1 mg to about 2.5 mg of one or more of the group consisting of folic acid, folinic acid, 6S)-tetrahydrofolic acid, 5-methyl-(6S)-tetrahydrofolic acid, 5-formyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid and the nutritionally acceptable salts thereof, and an amount of a citrated folic acid material containing about 1 mg to about 2.5 mg of folic acid, preferably about 1 mg of folic acid, about 400 IU to about 800 IU of Vitamin A,
about 20 mcg to about 625 mcg of Vitamin $B_1$,
about 400 mcg to about 600 mcg of Vitamin $B_{12}$,
about 30 mg to about 70 mg of Vitamin C,
about 1 mg to about 3 mg of elemental copper optionally administered in the form of a nutritionally acceptable copper amino acid chelate,
about 5 mg to about 15 mg of elemental zinc optionally administered in the form of a nutritionally acceptable zinc amino acid chelate,
in addition to the vitamins and minerals set forth above and a nutritionally acceptable carrier therefor.

In other exemplary embodiments of the present invention, nutritional supplements of the present invention consist of a daily dose (on a label claim basis) of:

about 90 mg of elemental iron administered in the form of an iron amino acid chelate prepared from aspartic acid and cysteine, about 1 mg of folic acid or an amount of a citrated folic acid material containing about 1 mg of folic acid, about 400 IU of Vitamin A administered as beta-carotene, about 25 mcg, about 125 mcg or about 625 mcg of Vitamin $B_1$ administered as thiamine pyrophosphate, about 25 mcg, about 125 mcg or about 625 mcg of Vitamin $B_2$ administered as flavin adenine dinucleotide hydrate, about 25 mcg, about 125 mcg or about 625 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as sodium ascorbate, about 2 mg of elemental copper optionally administered in the form of a copper amino acid chelate prepared according to the process of U.S. Pat. No. 7,341,708 using aspartic acid and lysine, about 10 mg of elemental zinc optionally administered in the form of a zinc amino acid chelate prepared according to the process of U.S. Pat. No. 7,341,708 using aspartic acid and lysine, about 5 mg of elemental magnesium administered as magnesium l-threonate, and a nutritionally acceptable carrier therefor.

The preferred form of administration of the nutritional supplements of the present invention are soft gelatin capsules, taken once daily in the amounts set forth above in the morning along with breakfast or after any early morning nausea in the case of pregnant women has passed. Optionally, the ingredients may be administered in two or more soft gelatin capsules where the various ingredients of the unique nutritional supplements of the present invention are separated into different soft gelatin capsules, which are taken at the same time or separately if desired. The capsules may be either liquid-filled or powder-filled, although the presently preferred dosage form is oil-based liquid-filled capsules.

DETAILED DESCRIPTION OF TILE INVENTION

Because of the blood formation requirements of the fetus and placenta, iron depletion and iron deficiency anemia make this the most common deficiency in pregnancy (90% of all anemias). Heme iron, which is derived from hemoglobin and myoglobin found in meats, is much better absorbed than non-heme, which is found mostly in foods of plant origin (30% versus 5% absorption). Women who are vegetarians absorb much less iron than that which is needed during pregnancy. Growth restriction, preterm delivery, and pre-eclampsia have been noted in women who have iron deficiency anemia. One of the problems with iron supplementation, in both women and men, is upper GI irritation resulting in nausea, vomiting and a decreased appetite as well as constipation. Thus, to mitigate both of these problems, the nutritional supplements of the present invention include about 50 mg/day to about 150 mg/day, preferably about 80 mg/day to about 100 mg/day, for example 90 mgs/day, of elemental iron preferably administered as an iron amino acid chelate. A presently preferred form of the iron material is an iron amino acid chelate, such as Amino-Ferr™, a form of iron containing pure chelated material without interfering ions, thus resulting in high solubility and adsorption. AminoFerr is a product of Viva Pharmaceuticals, Inc. of Richmond, British Columbia, Canada and is prepared according to the process of U.S. Pat. No. 7,341,708 (which is incorporated herein by this reference) using aspartic acid and cysteine. The AminoFerr has ferrous gluconate as a base or carrier during production, but the final product is without iron salt (that is, in pure iron amino acid chelate form) and is preferred for use in the nutritional supplements of the present invention. Other amino acids, such as those described in U.S. Pat. No. 7,341,708, for example at the top of column 4 thereof, can be used in the preparation of other iron amino acid chelates suitable for use in the present invention.

Folic acid is probably the most important vitamin during pregnancy. The requirement increases significantly in pregnancy and a deficiency of this vitamin is prevalent among American women. The cardinal result of folic acid deficiency is an increase in the open neural tube defect or spinal bifida. Also the risk of maternal anemia is significantly increased during pregnancy. It has been estimated that 2.5% to 5% of pregnant women in the United States are folic acid-deficient and this is particularly true in indigent patients, adolescents, or those having successive pregnancies with short intervals between them. A deficiency of folic acid results in fetal neural tube defects, preterm delivery, placental abruption and growth restricted fetuses. Since foods in this country are not fortified with folic acid, the nutritional supplements of the present invention include about 0.1 mg/day to about 5 mg/day, preferably about 1 mg/day to about 2.5 mg/day, for example about 1.0 mg/day, about 1.2 mg/day or about 2 mg/day, of one or more of the group consisting of folic acid, folinic acid, (6S)-tetrahydrofolic acid, 5-methyl-(6S)-tetrahydrofolic acid, 5-formyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid and the nutritionally acceptable salts thereof. Exemplary folic acid materials are about 1 mg of folic acid, a mixture of about 0.4 mg of citrated folic acid (controlled release) and about 0.8 mg of levo-folinic acid moiety as the sodium salt of 6(S)-5-formyl-tetrahydrofolic acid, and an amount of a citrated folic acid material containing about 1 mg of folic acid. Citrated folic acid can be prepared according to the methods described in co-pending application Ser. No. 14/053926, filed Oct. 15, 2013, in the name of Rhett Sean Daniels. The folic acid and the citrate buffer(s) need to be bound together with an appropriate binder for formulation into the nutritional supplements of the present invention. That citrated folic acid material may contain, for example, about 5% folic acid active, so in this example about 20 mg of citrated folic acid material would contain about 1 mg of folic acid. Other percentages of folic acid in the citrated folic acid material are possible.

Vitamin A plays an important role in maintaining the integrity of all epithelial tissues (skin/mucous membrane). It is also essential in the synthesis of retinal pigmentation and deficiency leads to a variety of ophthalmic problems. This vitamin is essential for normal fetal development and conversely deficiency leads to congenital malformations as well as fetal mortalities. Accordingly, the nutritional supplements of the present invention optionally include about 200 IU/day to about 2,000 IU/day, preferably about 400 IU/day to about 1,000 IU/day, for example about 400 IU/day or 600 IU/day or 800 IU/day of Vitamin A as beta-carotene, to supply the developing fetus with adequate amounts of this essential vitamin regardless of maternal diet. Each IU of beta-carotene corresponds to about 0.6 mcg of beta-carotene.

Vitamin $B_1$ is very important in red blood cell formation and all of the ingredients of fetal blood cells. Deficiency in the mother can result in acute fetal cardiac failure from significant anemia in the fetus. Since this vitamin is not ubiquitous in a normal diet, the supplements of the present invention include about 10 mcg/day to about 1,000 mcg/day of Vitamin $B_1$, for example about 25 mcg/per day to about 625 mcg/day, for example about 25 mcg/day, about 125 mcg/day or about 625 mcg/day, as thiamine (e.g., thiamine pyrophosphate) to enhance red blood cell formation.

The requirements for Vitamin $B_2$ increase during pregnancy. Deficiency has been associated with fetal malformation of the bony tissue and membranous skeleton, which precedes the cartilaginous and osseous skeletons. A deficiency of Vitamin $B_2$ is also linked to hyperemesis gravidarum and an increased incidence of growth restriction and preterm delivery in the fetus. Maternal deficiency of Vitamin $B_2$ is associated with stomatitis, glossitis and cheilosis. The supplements of the present invention optionally include about 10 mcg/day to about 1,000 mcg/day, for example about 25 mcg/day to about 625 mcg/day, for example about 25 mcg/day, about 125 mcg/day or about 625 mcg/day of Vitamin $B_2$ as flavin adenine dinucleotinde hydrate to mitigate any deficiency of this vital material.

Vitamin $B_3$ is necessary for appropriate fetal growth and for the proper functioning of cellular enzyme systems. In animals, small for gestational age offsprings are much more common when there is a deficiency of Vitamin $B_3$. Vitamin $B_3$ is also important for transforming carbohydrates into energy. The nutritional supplements of the present invention optionally include about 10 mcg/day to about 1,000 mcg/day, for example about 25 mcg/day to about 625 mcg/day, for example about 25 mcg/day, about 125 mcg/day or about 625 mcg/day, of nicotinamide adenine dinucleotide.

Vitamin $B_6$ (pyridoxine) is used by obstetricians to combat hyperemesis of pregnancy. During pregnancy $B_6$ levels in the plasma fall to as low as 25% of non-pregnant levels. This suggests there is an increased utilization of pyridoxine during gestation. Vitamin $B_6$ and folic acid have been shown to be associated with the lower risk of coronary artery disease particularly among women. While Vitamin $B_6$ is present in meat, whole grain breads and cereals as well as vegetables, it is particularly diminished among patients, both male and female, at high risk for inadequate nutrition (substance abuse, adolescents, short intervals between pregnancies, multi-fetal pregnancies, and women on restricted intake such as vegan diets). Among animals, Vitamin $B_6$ deficiency during pregnancy is associated with severe growth retardation, hypoplasia of the thymus and neonatal death as well as reduced immunologic competence. While there is no direct evidence of adverse effects of such deficiency in humans, volunteer studies among non-pregnant adults have shown that Vitamin $B_6$ deficiency can cause skin manifestations and some central nervous system defects. Further low levels tend to persist after pregnancy and during lactation and are also lower in cord blood and in the milk of such women. The nutritional supplements of the present invention optionally include about 0.5 mg/day to about 5 mg/day, for example about 1 mg/day, of Vitamin $B_6$ as pyridoxal 5' phosphate.

Vitamin $B_{12}$ is essential for appropriate folic acid metabolism, a deficiency of which is noted by megaloblastic anemia. It also plays a role in maintaining cellular integrity of the central nervous system. Therefore, while supplementation of folic acid may cure hematologic symptoms (anemia) of $B_{12}$ deficiency, it will leave the fetus vulnerable to central nervous system damage. Vitamin $B_{12}$ is found exclusively in animal tissues hence during pregnancy a vegan woman is at risk for $B_{12}$ deficiency. Accordingly, the nutritional supplements of the present invention include about 100 mcg/day to about 5,000 mcg/day of Vitamin $B_{12}$, or about 200 mcg/day to about 1,000 mcg/day, for example about 400 mcg/day to about 600 mcg/day, or about 500 mcg/day, for example in equal parts of 5'-deoxyadenosylcobalamin (about 250 mcg) and methylcobalamin (about 250 mcg), to mitigate any deficiency of this essential vitamin.

Vitamin C (ascorbic acid) is essential for the formation of collagen and therefore is very important for both mother and fetus during pregnancy. The transport mechanism across the placenta is the same for that of glucose therefore Vitamin C supplementation is very important in those women having (or at risk for) diabetes. There is a progressive drop in Vitamin C levels during each trimester and if serum levels of this ingredient drop below 80 mg/day habitual abortion, preterm birth and premature rupture of the membranes may occur. Since there are vagaries of absorption during pregnancy, the supplements of the present invention include about 10 mg/day to about 100 mg/day, preferably about 40 mg/day to about 60 mg/day, for example about 50 mg/day, of Vitamin C supplementation in the form of ascorbic acid or one or more nutritionally acceptably salts thereof (such as, for example, sodium ascorbate, magnesium ascorbate and/or zinc ascorbate).

Of all the trace elements, copper has received attention as probably being the most important in human gestation. The metabolism of this element is more altered by pregnancy than any other state. While serum copper rises during pregnancy, due to hormonal changes and protein binding efficiency, levels of copper are low in the fetus; therefore, it is important to supplement this trace element in the diet of pregnant women. Copper is also important as it is associated with a protein in the fetal mitochondria, which disappears shortly after birth. This mitochondrial function is important in most oxidative reactions in rapidly developing fetal tissues. The nutritional supplements of the present invention include about 1 mg/day to about 3 mg/day, preferably about 2 mg/day, of elemental copper to ensure that pregnant and nursing women have appropriate levels of copper during these important stages. Although any nutritionally acceptable source of copper will suffice, and many are generally known, a suitable copper material is a copper amino acid chelate that is a product of Viva Pharmaceuticals, Inc. of Richmond, British Columbia, Canada, which is prepared according to the process of U.S. Pat. No. 7,341,708 using aspartic acid and lysine. Other amino acids, such as those described in U.S. Pat. No. 7,341,708, for example at the top of column 4 thereof, can be used in the preparation of other copper amino acid chelates suitable for use in the present invention.

Zinc deficiency produces congenital malformations as well as fetal losses. Since maternal plasma levels of zinc decrease during pregnancy, supplementation is important. In the fetus deficiency of zinc may be involved with premature rupture of the membranes and a reduced ability to fight infection due to suppressed immunity. Zinc deficiency is quite common in the United States, particularly in pregnant women and, therefore, the nutritional supplements of the present invention include about 1 mg/day to about 30 mg/day, preferably about 5 mg/day to about 15 mg/day, or about 10 mg/day, of elemental zinc. Although any nutritionally acceptable source of zinc will suffice, and many are generally known, a suitable zinc material is a zinc amino acid chelate of Viva Pharmaceuticals, Inc. of Richmond, British Columbia, Canada, which is prepared according to the process of U.S. Pat. No. 7,341,708 using aspartic acid and lysine. Other amino acids, such as those described in U.S. Pat. No. 7,341,708, for example at the top of column 4 thereof, can be used in the preparation of other zinc amino acid chelates suitable for use in the present invention.

Magnesium deficiency has been linked to pre-eclampsia, premature rupture of the membranes and preterm births secondary to early labor. Women who deliver prematurely are more likely to have lower plasma levels of this mineral. The nutritional supplements of the present invention optionally include about 0.1 mg/day to about 10 mg/day, about 0.2 mg/day to about 5 mg/day, for example about 5 mg/day, of a magnesium salt administered, for example, as about 60 mg of magnesium 1-threonate that contains about 5 mg of elemental magnesium, to supplement any deficiencies that may occur.

Vitamin $B_1$, Vitamin $B_2$, Vitamin $B_3$ and Vitamin $B_{12}$ can be administered in mcg amounts, as shown above, if administered in "body ready" form, thus bypassing genetic defects that prevent vitamin absorption that is common in all people. The most reduced forms of vitamins decrease the likelihood that there would be inhibition of vitamin metabolism, and increase the likelihood that vitamin supplementation may be achieved in the face of genetic defects (sometimes referred to as genetic polymorphisms). Furthermore, by supplying minimally acceptable amounts of reduced forms of vitamins the chance of overdosing is decreased and the action of folate-iron nutritional supplements for the therapeutic indication (e.g., iron supplementation or prenatal supplementation) is not adversely affected.

All of the ingredients of the present invention are well known and are commercially available, generally from multiple sources (with the exception of citrated folic acid). Citrated folic acid can be prepared according to the methods set forth in co-pending application Ser. No. 14/053,926, filed Oct. 15, 2013, in the name of Rhett Sean Daniels. The iron amino acid chelate (e.g., AminoFerr), the copper amino acid chelate and the zinc amino acid chelate may be obtained from Viva Pharmaceuticals, Inc. of Richmond, British Columbia, Canada. The ingredients may be used in any chemical form known in the art to be suitable for use in nutritional supplements, except that, in certain instances as set forth above, particularly with regard to the preferred and particularly preferred embodiments of the present invention, specific forms are desired. In addition, the methods of manufacture thereof are well known to those skilled in this art (or is described in the above-identified provisional application) and need not be described further herein.

The nutritional supplements of the present invention include any suitable nutritionally acceptable carrier as would be known to one skilled in this art. The methods of nutritional formulation applicable to the supplements of the present invention are also well known to one skilled in this art and need not be described further herein. Suitable carriers and methods of formulation are shown, for example, in Remington's Pharmaceutical Sciences, (and other publications in the field of pharmaceutical or nutritional formulation), which to the extent necessary, are incorporated herein by this reference. Suitable carrier materials include, for example, citric acid, bovine gelatin, glycerin, glycine, hesperidin complex (a citrus bioflavinoid), 1-lysine acetate, 1-glutathione, lecithin, olive oil, purified water, tripotassium citrate, and yellow beeswax and various flavorings, such as caramel and orange flavorings. Any dosage form as appropriate may be utilized, although, given the nature of the ingredients described herein, soft gelatin capsules, using conventional nutritionally acceptable ingredients, are satisfactory and is the preferred form of administration, although other dosage forms may be used as well. A single daily capsule taken orally will suffice, generally to be taken at breakfast so as not to be forgotten during the day, although the daily dose may be split into two or more daily capsules if desired. The capsules may be either liquid-filled or powder-filled, although the presently preferred dosage form is oil-based liquid-filled capsules.

The embodiments of the present invention can be or are, as shown below in the Examples, free or substantially free of other added vitamins and minerals. For example, the nutritional supplements of the present invention do not include Vitamin Bs or Vitamin $B_7$; and do not include calcium at all or in other than trace or carrier quantities as might be present in certain carrier materials. Thus, the phrases "consisting essentially of" or "consisting of" should be construed as set forth in MPEP 2111.03 (Transitional Phrases). Those phrases and the phrase "free or substantially free of any other added vitamins and minerals" should be construed as precluding the presence of additional ingredients in nutritionally effective amounts (particularly those that are intentionally added in nutritionally effective amounts), but not preclude them in trace amounts or quantities that are present in other than nutritionally effective amounts, for example as part of the recited nutritionally acceptable carrier or as a minor impurity resulting from the production or manufacture of a recited material. Such a carrier will generally be, as is well known in this field, a multi-component carrier having many ingredients and the diluents, binders and adhesives, lubricants, plasticizers, disintegrants, colorants, bulking substances, flavorings, sweeteners, buffers, and adsorbents, that may include minerals in trace or carrier (but not nutritionally effective) quantities. The presence of such ingredients in trace or carrier quantities, for example in such a multi-component carrier or as a trace or minor impurity in a recited ingredient, is considered by Applicants to still be within the scope of claims having "consisting essentially of", "consisting of" and/or "free or substantially free of any other added vitamins and minerals" language, as long as nutritionally effective amounts or quantities of such ingredients are not intentionally added or used.

The following embodiments of the present invention as set forth in the Examples are each prepared as one or two soft gelatin capsules having the ingredients as shown (on a label claim basis) to be taken once or twice daily to supplement the nutritional diet of a person suffering from iron deficiency anemia.

EXAMPLES

Example 1

A nutritional supplement having a daily dose of:
about 90 mg of elemental iron administered in the form of an iron amino acid chelate prepared according to the process of U.S. Pat. No. 7,341,708 using aspartic acid and cysteine,
about 0.4 mg of citrated folic acid (controlled release) and about 0.8 mg of levo-folinic acid moiety as the sodium salt of 6(S)-5-formyl-tetrahydrofolic acid,
about 400 IU of Vitamin A administered as beta-carotene,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper administered as a copper amino acid chelate prepared according to the process of U.S. Pat. No. 7,341,708 using aspartic acid and lysine,
about 10 mg of elemental zinc administered as a zinc amino acid chelate prepared according to the process of U.S. Pat. No. 7,341,708 using aspartic acid and lysine,
about 5 mg of elemental magnesium administered as about 60 mg of magnesium l-threonate, and
a nutritionally acceptable carrier therefor.

Example 2

A nutritional supplement having a daily dose of:
about 90 mg of elemental iron administered in the form of an iron amino acid chelate prepared according to the process of U.S. Pat. No. 7,341,708 using aspartic acid and cysteine,
about 0.4 mg of citrated folic acid (controlled release) and about 0.8 mg of levo-folinic acid moiety as the sodium salt of 6(S)-5-formyl-tetrahydrofolic acid,
about 600 IU of Vitamin A administered as beta-carotene
about 125 mcg of Vitamin $B_1$ administered as thiamine pyrophosphate,
about 125 mcg of Vitamin $B_2$ administered as flavin adenine dinucleotide hydrate,
about 125 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium l-threonate, and
a nutritionally acceptable carrier therefor.

Example 3

A nutritional supplement having a daily dose of:
about 90 mg of elemental iron administered in the form of an iron amino acid chelate prepared according to the process of U.S. Pat. No. 7,341,708 using aspartic acid and cysteine,
about 0.4 mg of citrated folic acid (controlled release) and about 0.8 mg of levo-folinic acid moiety as the sodium salt of 6(S)-5-formyl-tetrahydrofolic acid,
about 800 IU of Vitamin A administered as beta-carotene
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc, and
a nutritionally acceptable carrier therefor.

Example 4

A nutritional supplement having a daily dose of:
about 90 mg of elemental iron administered in the form of an iron amino acid chelate prepared according to the process of U.S. Pat. No. 7,341,708 using aspartic acid and cysteine,
about 0.4 mg of citrated folic acid (controlled release) and about 0.8 mg of levo-folinic acid moiety as the sodium salt of 6(S)-5-formyl-tetrahydrofolic acid, about 25 mcg of Vitamin $B_1$ administered as thiamine pyrophosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, and a nutritionally acceptable carrier therefor.

Example 5

A nutritional supplement having a daily dose of:

about 90 mg of elemental iron administered in the form of an iron amino acid chelate prepared according to the process of U.S. Pat. No. 7,341,708 using aspartic acid and cysteine, about 0.4 mg of citrated folic acid (controlled release) and about 0.8 mg of levo-folinic acid moiety as the sodium salt of 6(S)-5-formyl-tetrahydrofolic acid, about 125 mcg of Vitamin $B_1$ administered as thiamine pyrophosphate, about 125 mcg of Vitamin $B_2$ administered as flavin adenine dinucleotide hydrate, about 125 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, and a nutritionally acceptable carrier therefor.

Example 6

A nutritional supplement having a daily dose of:

about 90 mg of elemental iron administered in the form of an iron amino acid chelate prepared according to the process of U.S. Pat. No. 7,341,708 using aspartic acid and cysteine, about 0.4 mg of citrated folic acid (controlled release) and about 0.8 mg of levo-folinic acid moiety as the sodium salt of 6(S)-5-formyl-tetrahydrofolic acid, about 600 IU of Vitamin A administered as beta-carotene about 125 mcg of Vitamin $B_1$ administered as thiamine pyrophosphate, about 500 mcg of Vitamin $B_{12}$ administered as about 250 mcg of 5'-deoxyadensosyl-cobalamin and about 250 mcg of methylcobalamin, about 5 omg of Vitamin C administered as about 56 mg of sodium ascorbate, about 2 mg of elemental copper, about 10 mg of elemental zinc, about 5 mg of elemental magnesium administered as about 60 mg of magnesium 1-threonate, and a nutritionally acceptable carrier therefor.

Example 7

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of citrated folic acid (controlled release) and about 1 mg of the calcium salt of 1-methylfolate [6(S)-5-methyltetrahydrofolate], about 400 IU of Vitamin A administered as beta-carotene, about 25 mcg of Vitamin $B_1$ administered as thiamine pyrophosphate, about 25 mcg of Vitamin $B_2$ administered as flavin adenine dinucleotide hydrate, about 25 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, about 5 mg of elemental magnesium administered as about 60 mg of magnesium 1-threonate, and a nutritionally acceptable carrier therefor.

Example 8

A nutritional supplement having a daily dose of:

about 90 mg of elemental iron administered in the form of an iron amino acid chelate prepared according to the process of U.S. Pat. No. 7,341,708 using aspartic acid and cysteine, about 1.2 mg of the calcium salt of 1-methylfolate [6(S)-5-methyltetrahydrofolate], about 400 IU of Vitamin A administered as beta-carotene, about 25 mcg of Vitamin $B_1$ administered as thiamine pyrophosphate, about 25 mcg of Vitamin $B_2$ administered as flavin adenine dinucleotide hydrate, about 25 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, about 5 mg of elemental magnesium administered as about 60 mgs of magnesium 1-threonate, and a nutritionally acceptable carrier therefor.

Example 9

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of folic acid, about 400 IU of Vitamin A administered as beta-carotene, about 25 mcg of Vitamin $B_1$ administered as thiamine pyrophosphate, about 25 mcg of Vitamin $B_2$ administered as flavin adenine dinucleotide hydrate, about 25 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper administered as a copper amino acid chelate prepared according to the process of U.S. Pat. No. 7,341,708 using aspartic acid and lysine, about 10 mg of elemental zinc administered as a zinc amino acid chelate prepared according to the process of U.S. Pat. No. 7,341,708 using aspartic acid and lysine, about 5 mg of elemental magnesium administered as about 60 mg of magnesium 1-threonate, and a nutritionally acceptable carrier therefor.

Example 10

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of folic acid, about 600 IU of Vitamin A administered as beta-carotene about 125 mcg of Vitamin $B_1$ administered as thiamine pyrophosphate, about 125 mcg of Vitamin $B_2$ administered as flavin adenine dinucleotide hydrate, about 125 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, about 5 mg of elemental magnesium as about 60 mg of magnesium 1-threonate, and a nutritionally acceptable carrier therefor.

Example 11

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of folic acid, about 800 IU of Vitamin A administered as beta-carotene about 625 mcg of Vitamin $B_1$ administered as thiamine pyrophosphate, about 625 mcg of Vitamin $B_2$ administered as flavin adenine dinucleotide hydrate, about 625 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, and a nutritionally acceptable carrier therefor.

Example 12

A nutritional supplement having of a daily dose of about 90 mg of elemental iron administered in the form of an iron amino acid chelate prepared according to the process of U.S. Pat. No. 7,341,708 using aspartic acid and cysteine, about 1 mg of folic acid, about 25 mcg of Vitamin $B_1$ administered as thiamine pyrophosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, and a nutritionally acceptable carrier therefor.

Example 13

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of folic acid, about 125 mcg of Vitamin $B_1$ administered as thiamine pyrophosphate, about 125 mcg of Vitamin $B_2$ administered as flavin adenine dinucleotide hydrate, about 125 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc, about 5 mg of elemental magnesium administered as about 60 mg of magnesium 1-threonate, and a nutritionally acceptable carrier therefor.

Example 14

A nutritional supplement having a daily dose of:

about 90 mg of elemental iron administered in the form of an iron amino acid chelate prepared according to the process of U.S. Pat. No. 7,341,708 using aspartic acid and cysteine, about 1 mg of folic acid, about 600 IU of Vitamin A administered as beta-carotene about 125 mcg of Vitamin $B_1$ administered as thiamine pyrophosphate, about 500 mcg of Vitamin $B_{12}$ administered as about 250 mcg of 5'-deoxyadensosyl-cobalamin and about 250 mcg of methylcobalamin, about 50 mg of Vitamin C administered as about 56 mg of sodium ascorbate, about 2 mg of elemental copper, about 10 mg of elemental zinc,
about 5 mg of elemental magnesium administered as about 60 mg of magnesium 1-threonate, and
a nutritionally acceptable carrier therefor.

Example 15

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 600 IU of Vitamin A administered as beta-carotene,
about 125 mcg of Vitamin $B_1$ administered as thiamine pyrophosphate,
about 125 mcg of Vitamin $B_2$ administered as flavin adenine dinucleotide hydrate,
about 125 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium 1-threonate, and
a nutritionally acceptable carrier therefor.

Example 16

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium 1-threonate, and
a nutritionally acceptable carrier therefor.

Example 17

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

Example 18

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium 1-threonate, and
a nutritionally acceptable carrier therefor.

Example 19

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper, about 10 mg of elemental zinc,
about 5 mg of elemental magnesium administered as about 60 mg of magnesium l-threonate, and
a nutritionally acceptable carrier therefor.

Example 20

A nutritional supplement having a daily dose of:
about 90 mg of elemental iron administered in the form of an iron amino acid chelate prepared according to the process of U.S. Pat. No. 7,341,708 using aspartic acid and cysteine,
an amount of citrated folic acid material containing about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium l-threonate, and
a nutritionally acceptable carrier therefor.

Example 21

A nutritional supplement having a daily dose of:
about 90 mg of elemental iron administered in the form of an iron amino acid chelate prepared according to the process of U.S. Pat. No. 7,341,708 using aspartic acid and cysteine,
an amount of citrated folic acid containing about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 5 mg of elemental magnesium administered as about 60 mg of magnesium l-threonate, and
a nutritionally acceptable carrier therefor.

Example 22

A nutritional supplement having a daily dose of:
about 90 mg of elemental iron administered in the form of an iron amino acid chelate prepared according to the process of U.S. Pat. No. 7,341,708 using aspartic acid and cysteine,
an amount of citrated folic acid containing about 1 mg of folic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc,
about 5 mg of elemental magnesium administered as about 60 mg of magnesium l-threonate, and
a nutritionally acceptable carrier therefor.

Example 23

A nutritional supplement having a daily dose of:
about 90 mg of elemental iron administered in the form of an iron amino acid chelate prepared according to the process of U.S. Pat. No. 7,341,708 using aspartic acid and cysteine,
an amount of citrated folic acid containing about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as sodium ascorbate,
about 2 mg of elemental copper,
about 10 mg of elemental zinc,
about 5 mg of elemental magnesium administered as magnesium l-threonate, and
a nutritionally acceptable carrier therefor.

Example 24

A nutritional supplement having a daily dose of:
about 90 mg of elemental iron administered in the form of an iron amino acid chelate prepared according to the process of U.S. Pat. No. 7,341,708 using aspartic acid and cysteine,
about 1 mg of folic acid,
about 800 IU of Vitamin A administered as beta-carotene,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin, about 50 mg of Vitamin C administered as sodium ascorbate, about 2 mg of elemental copper, about 10 mg of elemental zinc, about 5 mg of elemental magnesium administered as magnesium l-threonate, and a nutritionally acceptable carrier therefor.

Examples: 25-28

Examples 9, 13, 15 and 19 are repeated using an amount of a citrated folic acid material containing about 1 mg of folic acid in place of the about 1 mg of folic acid in each Example. For example, about 20 mg of a citrated folic acid material containing 5% folic acid (that is, about 1 mg of folic acid) is used in place of the about 1 mg of folic acid in each of Examples 9, 13, 15 and 19.

Exemplary nutritionally acceptable carriers are a combination of annatto (for color), citric acid, gelatin, glycerin, sunflower lecithin, natural orange (for flavor), olive oil, purified water, and yellow beeswax in amounts suitable for formulating the supplements of the present invention as liquid-filled soft gelatin capsules; a combination of glycine, L-lysine acetate, L-glutathione, hesperidin complex, tripotassium citrate, citric acid, olive oil, sunflower lecithin and yellow beeswax in amounts suitable for formulating the supplements of the present invention as liquid-filled soft gelatin capsules; and a combination of caramel, citric acid, gelatin, glycerin, glycine, hesperidin complex, L-lysine acetate, L-glutathione, sunflower lecithin, natural orange (for flavor), olive oil, purified water, tripotassium citrate, and yellow beeswax in amounts suitable for formulating the supplements of the present invention as liquid-filled soft gelatin capsules. Other vegetable oils can be substituted for the olive oil in the above exemplary nutritionally acceptable carriers.

The nutritional supplements of the present invention can be or are, as shown in the above Example, free or substantially free of other added vitamins and minerals (as those words have been defined above). Additionally, the embodiments of the present invention can be or are, as shown in the above Examples, free or substantially free of pharmaceutically active agents (in this regard, the ingredients in the supplements of the present invention are considered nutritional agents and not pharmaceutically active agents).

The nutritional supplements of the present invention should be manufactured in accordance with the Current Good Manufacturing Practices in Manufacturing, Packaging, Labeling and Holding Operations for Dietary Supplements as promulgated by the Federal Food and Drug Administration, as the same may be amended from time to time, and other applicable regulations. It has been found that, when providing multiple vitamins in a dietary or nutritional supplement, some degradation of certain of the vitamins may occur over time. Accordingly, the manufacturing specifications for the vitamins should be about 100% to about 175%, preferably about 100% to about 160%, of the dosage amounts set forth above with respect to various embodiments of the present invention. The manufacturing specifications for the other ingredients should be about 100% to 135%, preferably about 100% to about 130%, of the dosage amounts set forth above with respect to various embodiments of the present invention.

While various embodiments of the present invention have been described, it should be understood that various modifications and adaptations thereof will be apparent to one skilled in this art. Such modifications and adaptations are considered to be within the scope of the present invention, which is limited only by the scope of the following claims.

What is claimed is:

1. A nutritional supplement for supplementing the daily nutritional diet of a person having iron deficiency anemia consisting of a daily dose (all on a label claim basis) of:

about 90 mg of elemental iron administered in the form of an iron amino acid chelate prepared using aspartic acid and cysteine, about 1 mg of folic acid or an amount of a citrated folic acid material containing about 1 mg of folic acid, about 800 IU of Vitamin A administered as beta-carotene about 625 mcg of Vitamin $B_1$ administered as thiamine pyrophosphate, about 625 mcg of Vitamin $B_2$ administered as flavin adenine dinucleotide hydrate, about 625 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as sodium ascorbate, about 2 mg of elemental copper, about 10 mg of elemental zinc, about 5 mg of elemental magnesium administered as magnesium l-threonate, and a nutritionally acceptable carrier therefor.

2. The supplement of claim 1 wherein the supplement is free or substantially free of other minerals and vitamins in nutritionally effective amounts.

3. The supplement of claim 1 wherein the supplement has about 1 mg of folic acid.

4. The supplement of claim 1 wherein the supplement has an amount of a citrated folic acid material containing about 1 mg of folic acid.

5. A method of supplementing the daily nutritional diet of a person having iron deficiency anemia comprising orally administering to such person the supplement of claim 3.

6. A method of supplementing the daily nutritional diet of a person having iron deficiency anemia comprising orally administering to such person the supplement of claim 4.

7. A method of supplementing the daily nutritional diet of a person having iron deficiency anemia comprising orally administering to such person the supplement of claim 1.

8. The supplement of claim 2 wherein the supplement has about 1 mg of folic acid.

9. The supplement of claim 2 wherein the supplement has an amount of a citrated folic acid material containing about 1 mg of folic acid.

10. A method of supplementing the daily nutritional diet of a person having iron deficiency anemia comprising orally administering to such person the supplement of claim 2.

* * * * *